United States Patent
Zhang et al.

(10) Patent No.: US 9,982,019 B2
(45) Date of Patent: May 29, 2018

(54) GLYCOPEPTIDE COMPOUND OR PHARMACEUTICAL SALT THEREOF AND METHOD FOR PREPARING SAME, AND PHARMACEUTICAL COMPOSITIONS AND APPLICATIONS THEREOF

(71) Applicants: Zhejiang Medicine Co., Ltd. Xinchang Pharmaceutical Factory, Xinchang County (CN); Shanghai Health Creation Center Ltd. For Biopharmaceuticals R & D, Shanghai (CN); Shanghai Institute Of Pharmaceutical Industry, Shanghai (CN)

(72) Inventors: Dingfeng Zhang, Xinchang County (CN); Yuanyuan Ge, Xinchang County (CN); Mei Ge, Xinchang County (CN); Weicheng Zhou, Xinchang County (CN); Wei Wei, Xinchang County (CN); Shunli Zhang, Xinchang County (CN); Lingao Ruan, Xinchang County (CN); Zhenren Liu, Xinchang County (CN); Chang Shao, Xinchang County (CN)

( * ) Notice: Subject to any disclaimer, the term of this patent is extended or adjusted under 35 U.S.C. 154(b) by 0 days. days.

(21) Appl. No.: 14/655,830

(22) PCT Filed: Dec. 26, 2013

(86) PCT No.: PCT/CN2013/001647
§ 371 (c)(1),
(2) Date: Jun. 26, 2015

(87) PCT Pub. No.: WO2014/101294
PCT Pub. Date: Jul. 3, 2014

(65) Prior Publication Data
US 2015/0353607 A1 Dec. 10, 2015

(30) Foreign Application Priority Data
Dec. 27, 2012 (CN) .......................... 2012 1 0581733

(51) Int. Cl.
*C07K 9/00* (2006.01)
*C07K 11/00* (2006.01)
(Continued)

(52) U.S. Cl.
CPC .............. *C07K 9/006* (2013.01); *C07K 9/008* (2013.01); *A61K 38/00* (2013.01); *C07K 11/00* (2013.01);
(Continued)

(58) Field of Classification Search
None
See application file for complete search history.

(56) References Cited

PUBLICATIONS

Pavlov et al. A new type of chemical modification of glycopeptides antibiotics: aminomethylated derivatives of eremomycin and their antibacterial activity. J Antibiot (Tokyo). Jun. 1997;50(6):509-13.*
(Continued)

*Primary Examiner* — Satyanarayana R Gudibande
*Assistant Examiner* — Jia-Hai Lee
(74) *Attorney, Agent, or Firm* — Ash Tankha; Lipton, Weinberger & Husick

(57) ABSTRACT

The present invention provides a glycopeptide compound or pharmaceutically acceptable salt thereof as shown in Formula (I) or (II), and a method for preparing same, and pharmaceutical compositions and applications thereof, wherein the definition of $R_1$, $R_2$, $R_3$, $R_4$, $R_5$ is the same as that of the specification. The glycopeptide compound of the present invention has in-vitro antibacterial activity and has important significance for development of new antibacterial agents.

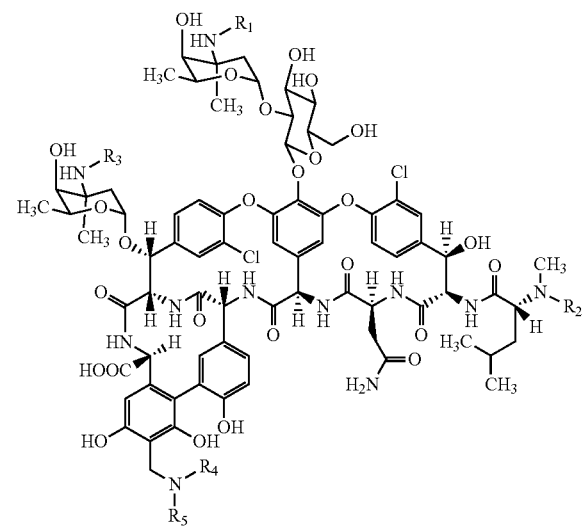

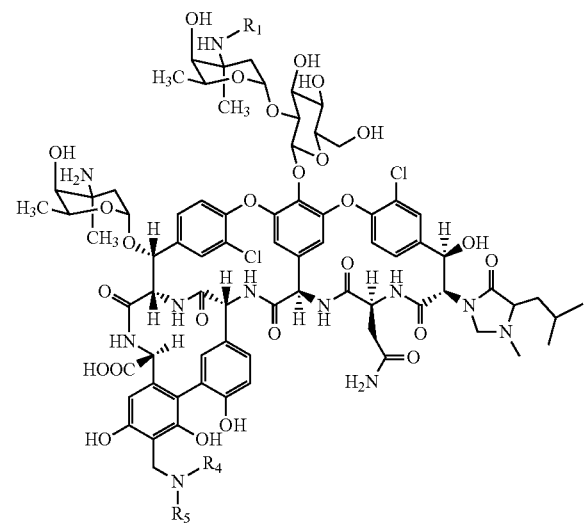

12 Claims, No Drawings

(51) Int. Cl.
    *C07K 14/00* (2006.01)
    *C07K 11/02* (2006.01)
    *A61K 38/00* (2006.01)
(52) U.S. Cl.
    CPC ............ *C07K 11/02* (2013.01); *C07K 14/001* (2013.01); *Y10S 930/19* (2013.01)

(56) References Cited

PUBLICATIONS

Shao et al. Synthesis and antibacterial activity of N4-mono alkyl derivatives of novel glycopeptide LYV07ww01. Bioorg. Med. Chem. Lett. 21 (2011) 6732-6738.*

* cited by examiner

GLYCOPEPTIDE COMPOUND OR PHARMACEUTICAL SALT THEREOF AND METHOD FOR PREPARING SAME, AND PHARMACEUTICAL COMPOSITIONS AND APPLICATIONS THEREOF

CROSS-REFERENCE TO RELATED APPLICATIONS le;3qThis application is a national phase application of the PCT international application number PCT/CN2013/001647 titled "Glycopeptide Compound Or Pharmaceutical Salt Thereof And Method For Preparing Same, And Pharmaceutical Compositions And Applications Thereof", filed in the State Intellectual Property Office of the People's Republic of China on Dec. 26, 2013, which claims priority to and the benefit of Chinese patent application number 201210581733.X, filed in the State Intellectual Property Office of the People's Republic of China on Dec. 27, 2012. The specifications of the above referenced patent applications are incorporated herein by reference in their entirety.

FIELD OF THE INVENTION

The present invention relates to a field of pharmaceutical chemistry synthesis, in particular, relates to glycopeptide derivatives with Mannich side-link and method for preparing the same and pharmaceutical compound and applications thereof.

BACKGROUND OF THE INVENTION

Glycopeptide antibiotics is the first choice pharmaceutical for clinically treating infection of methicillin-resistant *Staphylococcus aureus* (MRSA). However, the treatment MRSA of using Glycopeptide antibiotics causes developments of bacterial drug resistance, for example sensibility of MRSA against vancomycin is reduced. It will produce serious risks to clinically treat infection. Therefore, it is extremely urgent to find new glycopeptide antibiotics of effective drug-resistant strains.

A Chinese Patent Application No. 200910053906.9 reports that a new type of glycopeptide compound LYV07ww01 has antibacterial activity, its novelty lies in that a hydroxyl at position 4 of amino acid sugar at position 6 of peptide backbone is a axial bond.

A Chinese Patent Application No. 201110070597.3 reports that synthesis and antibacterial activities of three-substituted derivatives on N1, N4, N6 three amino acid residues based on compound LYV07ww01.

A Chinese Patent Application No. 201110070599.2 reports that synthesis and antibacterial activities of mono-substituted derivatives on amino acid residues based on LYV07ww01 compound. It have been found from the study that the activity of N4-alkyl compounds is the best, the activity of N1, N4-dialkyl compound is the second, and N1, N4, N6—three alkyl compound does not have obvious activity.

SUMMARY OF THE INVENTION

The present invention synthesizes derivatives and testing the antimicrobial activity, based on a Mannich reaction at a resorcinol position of 7-amino acid residues of N4-single alkyl compound.

A purpose of the present invention is to provide various of glycopeptide derivatives of formula (I) or (II) or pharmaceutically acceptable salts thereof.

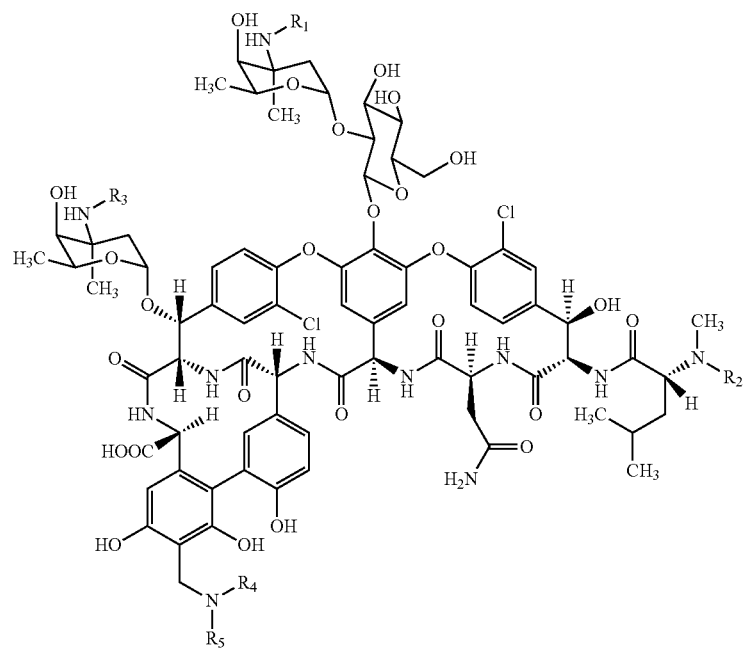

I

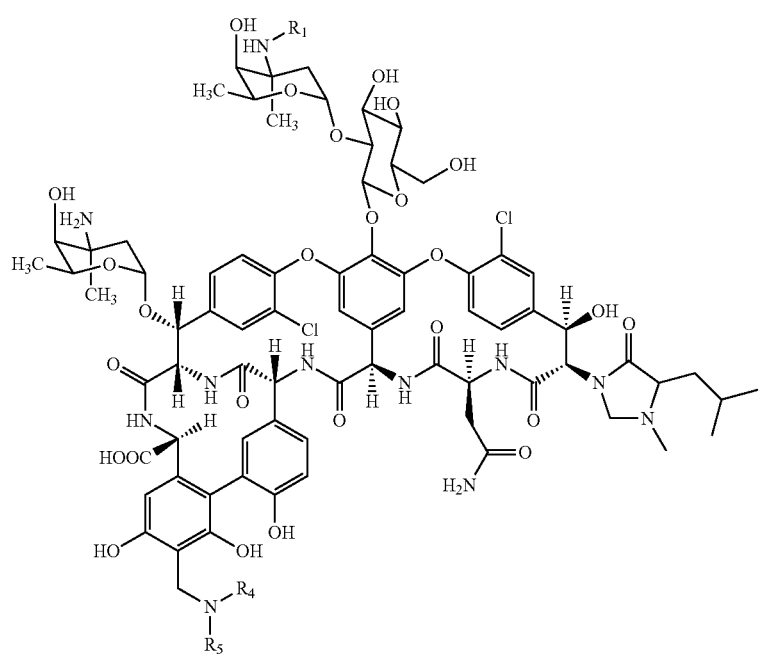

Wherein:

R1 is H, n-decyl, or a mono-substituted benzyl substituted by halogen, methoxy or isopropyl;

R2 is H, fluorenylmethoxycarbonyl or n-decyl;

R3 is H or n-decyl;

NR4R5 is diethylamino, n-butylamino, morpholino, or phosphonic acid methylene amino.

According to glycopeptide compounds or pharmaceutically acceptable salts thereof of the present invention, preferable a hydroxyl at position 4 of amino acid sugar at position 6 of peptide backbone is a axial bond.

According to glycopeptide compounds or pharmaceutically acceptable salts thereof of the present invention, preferable, a mono-substituted benzyl is 2-bromobenzyl, 3-bromophenyl, 4-bromobenzyl, 4-isopropylbenzyl, or 4-methoxybenzyl.

Another purpose of the present invention is to provide a method for preparing compounds of formula (I) or (II) or pharmaceutically acceptable salts thereof, the compound of formula (I) or (II) or pharmaceutically acceptable salt thereof of the present invention may be prepared by a synthetic route as follows.

A. Synthesis of compound with formula (I)

A resorcinol structure of 7-amino acid residue of compound of formula (III) undergoes a Mannich reaction to produce a compound of formula (I) or pharmaceutically acceptable salt thereof, comprising

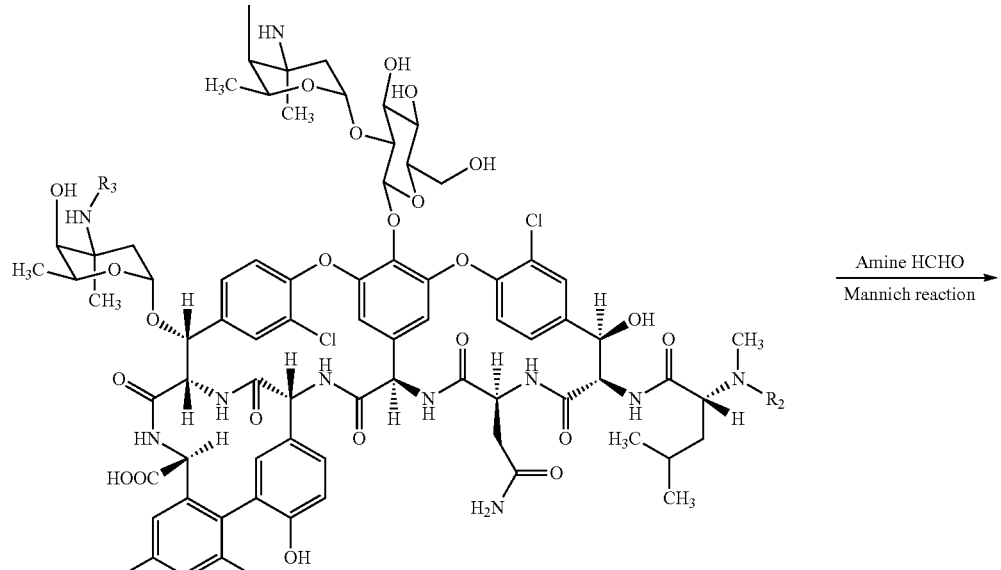

-continued

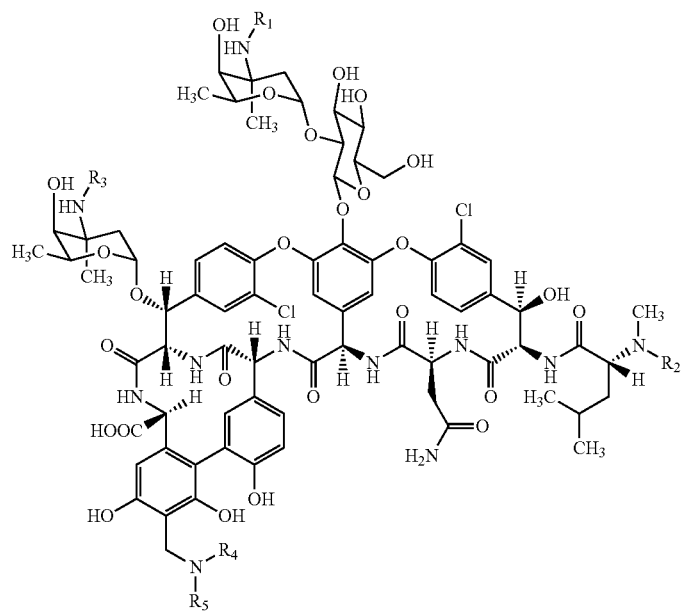

I

Compound of formula (III) reacts with formaldehyde,

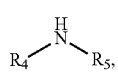

and N,N-diisopropylethylamine in an organic solvent at a temperature of 0° C.~35° C. to produce compound of formula (I). Wherein, R1 is H, n-decyl or mono-substituted benzyl substituted by halogen, methoxy or isopropyl; R2 is H, Wat methoxycarbonyl or n-decyl; R3 is H or n-decyl; NR4R5 is diethylamino, n-butylamino, morpholino, phosphonic acid methylene amino.

Preferably, a molar ratio of formaldehyde to compound of formula (III) is 1:1~5:1, and a molar ratio of amine to compound of formula (III) is 1:1~7:1, and a molar ratio of N, N-diisopropylethylamine to compound of formula (III) is 0:1~15:1. More preferably, a molar ratio of formaldehyde to compound of formula (III) is 1:1~1.2:1, and a molar ratio of amine to compound of formula (III) is 1.1:1, and a molar ratio of N, N-diisopropylethylamine to compound of formula (III) is 14:1.

Preferably, the mono-substituted benzyl is 2-bromobenzyl, 3-bromophenyl, 4-bromobenzyl, 4-isopropylbenzyl, 4-methoxybenzyl.

Preferably, the organic solvent is selected from the group consisting of C1~C4 alcohols, acetonitrile, water; the temperature is 15° C.~25° C. C1~C4 alcohol is methanol, ethanol, propanol, butanol, or n-butanol.

More preferably, a volume ratio of acetonitrile to water in the organic solvent is 1:1.

The synthetic method of compound of formula (III) refers to Chinese Patent Application No. 201110070599.2 and 201110070598.8.

B. Synthesis of Compound of Formula (II)

The method of synthesizing compound of formula (II) or pharmaceutically acceptable salt thereof from compound of formula (IV) through a Mannich reaction comprises the steps as follows:

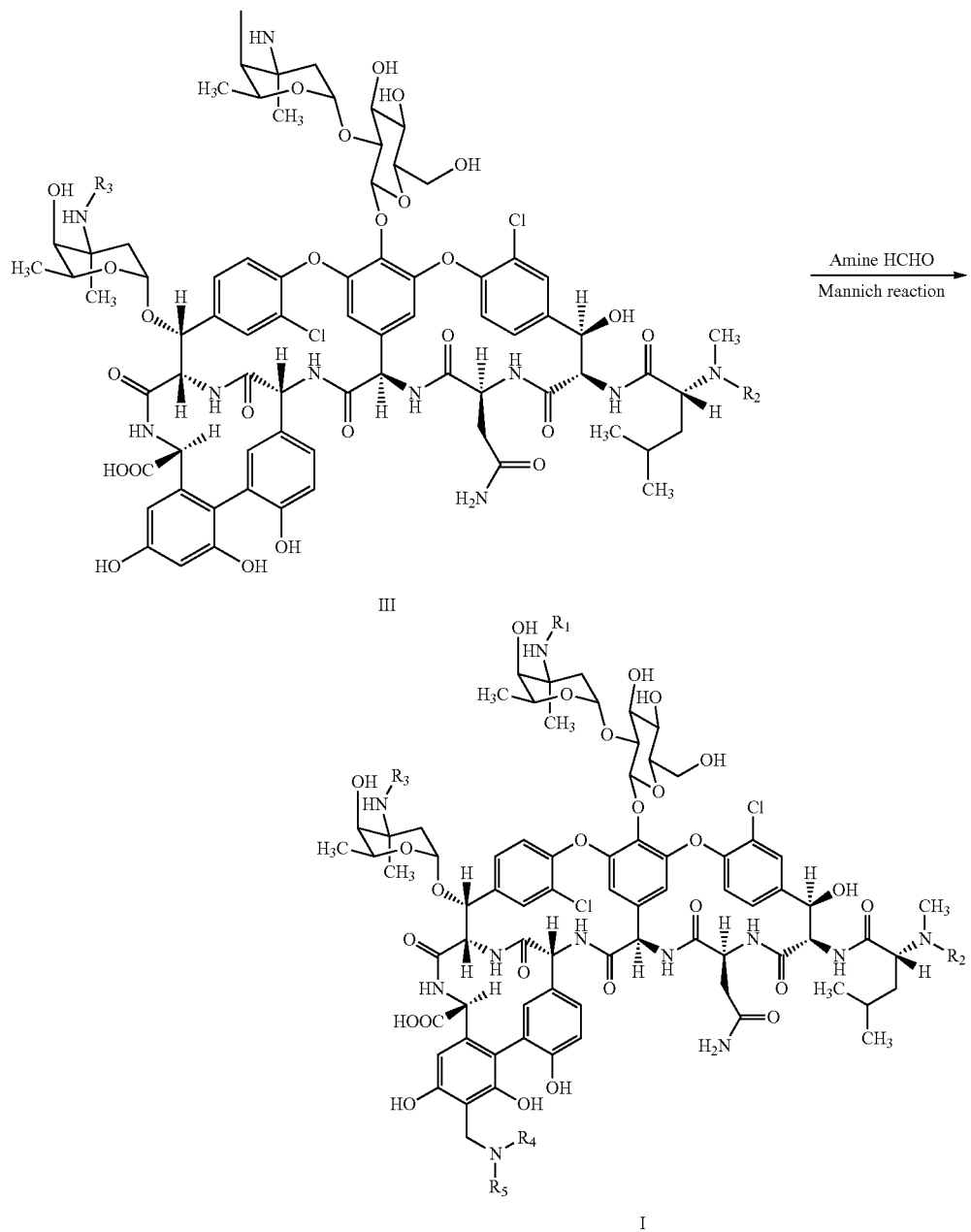

Compound of formula (IV) reacts with formaldehyde, amines

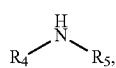

and N,N-diisopropylethylamine in an organic solvent at a temperature of 0° C.~35° C. to produce a compound of formula (II). Wherein, R1 is H or n-decyl, or mono-substituted benzyl substituted by halogen, methoxy or isopropyl; NR4R5 is diethylamino, n-butylamino, morpholino or phosphonic acid methylene amino.

Preferably, a molar ratio of formaldehyde to compound of formula (IV) is 1:1~10:1, a molar ratio of amine to compound of formula (IV) is 1:1~6:1, and a molar ratio of N, N-diisopropylethylamine to compound of formula (IV) is 0:1~14:1. More preferably, a molar ratio of formaldehyde to compound of formula (IV) is 3:1~6:1, a molar ratio of amine to compound of formula (IV) is 1.2:1, a molar ratio of N, N-diisopropylethylamine to compound of formula (IV) is 14:1.

Preferably, the mono-substituted benzyl is 2-bromobenzyl, 3-bromophenyl, 4-bromobenzyl, 4-isopropylbenzyl, or 4-methoxybenzyl.

Preferably, the organic solvent is selected from the group consisting of C1~C4 alcohol, acetonitrile, water, the temperature is 15° C.~25° C. More preferably, a volume ratio of acetonitrile to water in the organic solvent is 1:1. C1~C4 alcohol is methanol, ethanol, propanol, butanol, or n-butanol.

The synthetic method of the compound of formula (IV) refers to the Chinese Patent No. 201110070598.8.

A further purpose of the present invention is to provide a pharmaceutical composition comprising a therapeutically effective amount of glycopeptide derivatives or pharmaceutically acceptable salts thereof and a pharmaceutically acceptable carrier. The pharmaceutically acceptable carrier of the present invention refers to a conventional pharmaceutical carrier in pharmaceutical fields, for example, diluents, excipients (such as water, etc.), binder (such as cellulose derivatives, gelatin, polyvinyl pyrrolidone, etc.), fillers (such as starch, etc.), cracking agents (such as calcium carbonate, sodium bicarbonate). Furthermore, other adjuvants such as sweeteners, flavoring agents etc. may also be added into the composition.

The pharmaceutical composition of the present invention may be applied to patients to need treatment by intravenous injection, subcutaneous injection or oral administration. As for oral administration, it may be prepared into conventional solid preparations such as tablets, powders, capsules and so on. As for injection, it may be prepared into injection. Various of forms of the pharmaceutical composition of the present invention may be prepared by a conventional method of pharmaceutical fields. Wherein a content of the active ingredient is 0.1 wt. %~99.5 wt. %. A content of the compound of the present invention is 0.1 wt. %~99.5 wt. % in the preparation, preferable, the content is 0.5 wt. % 90 wt. %.

A general dose of the pharmaceutical composition applied to a patient to need treatment may refer to a existing dose of vancomycin and norvancomycin, for example, adults may be 0.1~2.0 g/d, and depends on changes of age and condition of a patient. The compound of the present invention may salify by a conventional method, for example, a hydrochloride salt.

Another purpose of the present invention is to provide an application of the compound for preparation of a medicament against bacterial infection. The beneficial effect of the present invention lies in the compound of formula (I) or (II) having good antibacterial effects.

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Example 1

Synthesis of Compound $I_1$

In ice-water bath (0° C.), amino methane phosphonic acid (140 mg, 1.26 mmol) is dissolved in 3 ml water, then DIEA (0.2 ml, 1.26 mmol) and 3 ml acetonitrile is added. 37% formaldehyde aqueous solution (15 μl, 0.18 mmol) is added into the above solution, and compound (III) (300 mg, 0.18 mmol) ($R_1$=H, $R_2$=H, $R_3$=H, refers to the synthesis method of the Chinese Patent Publication No. CN 101928331 A) and DIEA (0.2 ml, 1.26 mmol) are added for 15 min. The reaction is proceeding at room temperature of 25° C. for 3 h and then stopped. The reaction solution is adjusted to neutral with 20% TFA solution in a ice bath, and an appropriate amount of acetonitrile is added, to produce precipitate and then filtered to obtain a filter cake. A filter cake is washed with acetonitrile for several times, and purified by preparative HPLC by using an aqueous solution containing 0.1% HCOOH and methanol as a mobile phase, to obtain component by distilling off methanol under a reduced pressure, and adjusted pH 6-7 with saturated NaHCO3 aqueous solvent, and separated by gel column by using water as a mobile phase, and then obtain component by distilling off water under a reduced pressure, and dried in vacuum to obtain a solid compound $I_1$ 130 mg, the yield is 42.2%. (refer to Table 1)

Compound $I_1$: $^1$H-NMR (400 MHz, DMSO-$d_6$+$D_2O$) δ(ppm): 7.80 (1H), 7.67-7.60 (2H), 7.40 (2H), 7.15-6.98 (4H), 6.50 (2H), 5.61-5.39 (6H), 5.27-5.24 (2H), 5.06 (1H), 4.44-4.41 (3H), 4.30 (2H), 4.07-4.06 (2H), 3.77-3.59 (6H), 3.41 (3H), 2.97-2.94 (2H), 2.64-2.58 (2H), 2.42 (3H), 2.30-2.21 (2H), 2.00 (2H), 1.71-1.60 (5H), 1.35-1.33 (10H), 0.91 (6H).

Example 2

Synthesis of Compound $I_2$

At room temperature 20° C., 10 ml methanol is added into a 100 ml eggplant-shaped flask, then 1 mmol/ml morpholine (0.23 ml, 0.23 mmol) and DIEA (0.1 ml, 0.63 mmol) are added under stirring, and then 1 mmol/ml formaldehyde solution (0.21 ml, 0.21 mmol) is added, then stir for 15 min. compound (III) (300 mg, 0.18 mmol) ($R_1$=H, $R_2$=H, $R_3$=H, refer to the synthesis method of the Chinese Patent Publication No. CN 101928331 A) and DIEA (0.1 ml, 0.63 mmol) are added into the above solution, and stir at room temperature for 3 h when the addition is completed. 70 ml acetone is added under stirring to produce white insoluble precipitate and then filtered to obtain a filter cake. The filter cake is washed with acetone after filtered to obtain a white solid, then purified by preparative HPLC, by using an aqueous solution containing 0.1% HCOOH and methanol as a mobile phase to gradient elution with detection wavelength of 240 nm and 280 nm, a flow rate 22 ml/min. The fractions are concentrated into about 20 ml under a reduced pressure, and then adjusted to pH 6-7 by a saturated sodium bicarbonate solution, and extracted by adding an equal volume of n-butanol, and an organic layer is separated and washed with water (10 ml×2), and evaporated to dryness solvent under a reduced pressure to produce a residue, the residue is stirred overnight after adding methylene chloride, and then filtered, and dried at 45° C. to obtain 30 mg compound $I_2$ (a free base, white powder), and the yield is 9.3%. (refer to Table 1)

Compound $I_2$: 1H-NMR (400 MHz, DMSO-d6+D2O) δ(ppm): 7.90-8.31 (2H), 7.54-7.80 (2H), 7.35-7.11 (4H), 7.12 (2H), 6.75 (2H), 6.47 (1H), 5.68-5.55 (2H), 5.45-4.98 (5H), 4.74 (2H), 4.65-4.43 (3H), 3.76 (2H), 3.64 (4H), 3.45 (2H), 3.00-3.50 (6H), 2.33 (5H), 2.02-1.46 (5H), 1.28-1.02 (10H), 0.94-0.79 (6H).

Example 3

Synthesis of the Compound $I_3$

At room temperature 25° C., 10 ml n-butanol is added into 50 ml eggplant-shaped flask, then 1 mmol/ml n-butylamine solution (0.12 ml, 1.2 mmol) and 1 mmol/ml formaldehyde solution (0.25 ml, 1.0 mmol) are added and stirred for 15 min after the addition is completed. compound (III) (320 mg, 0.2 mmol) ($R_1$=H, $R_2$=H, $R_3$=H, refer to the synthesis method of the Chinese Patent Publication No. CN 101928331 A) is added into the above solution and stirred at room temperature 15-25° C. for 3 h after the addition is completed. 70 ml of acetone is added thereto under stirring, to produce white insoluble precipitate and then filtered to obtain a filter cake., the filter cake is washed with acetone to produce a white solid, then purified by preparative HPLC, using an aqueous solution containing 0.1% HCOOH and methanol as a mobile phase to gradient elution with detection wavelength of 240 nm and 280 nm, a flow rate 22 ml/min. The fractions are concentrated under a reduced pressure to about 20 ml, and then adjusted to pH 6-7 by a saturated sodium bicarbonate solution, then extracted by adding an equal volume of n-butanol, and an organic layer is separated and washed with water (10 ml×2), and evaporated to dryness solvent under a reduced pressure to produce a residue, the residue is stirred overnight after adding methylene chloride, after filtering, dried on 45° C. to obtain 35 mg compound $I_3$, and the yield is 9.8%. (refer to Table 1)

Compound $I_3$: 1H-NMR (400 MHz, DMSO-d6+D2O) δ(ppm): 7.90-8.31 (2H), 7.54-7.80 (2H), 7.35-7.11 (4H), 7.12 (2H), 6.75 (2H), 6.47 (1H), 5.68-5.55 (2H), 5.45-4.98 (5H), 4.74 (2H), 4.65-4.43 (3H), 3.76 (2H), 3.64 (4H), 3.45 (2H), 3.00-3.50 (6H), 2.33 (5H), 2.02-1.46 (5H), 1.28-1.02 (10H), 0.94-0.79 (6H).

Example 4

Synthesis of the Compound $I_4$

At room temperature 25° C., n-butylamine (14.1 μl, 0.14 mmol) is dissolved in 3 ml water, and DIEA (0.35 ml, 2.10 mmol) and 3 ml acetonitrile are added. 37% formaldehyde aqueous solution (10.5 μl, 0.14 mmol) is added by pipette, compound (III) (300 mg, 0.14 mmol) ($R_1$=n-decyl, $R_2$=n-decyl, $R_3$=n-decyl, refers to the synthesis method of the Chinese Patent Application No. 201110070599.2) is added after 15 min, and placed in an oil bath at 30° C. Then the reaction is stopped after 23 h 30 min. The reaction solution is adjusted to neutral with 3 mol/L HCl solution, an appropriate amount of acetone is added, and produce white insoluble precipitate and then filtered to obtain a filter cake, the filter cake is washed with acetone for several times, and purified by preparative HPLC, using the aqueous solution containing 0.1% HCOOH and methanol as the mobile phase, the obtained components is distilled off methanol under a reduced pressure, and then adjusted pH6-7 with a saturated aqueous NaHCO3, then separated by gel column, with water as a mobile phase, and distilled off the water under a reduced pressure, and dried in vacuum to obtain 152 mg solid 14, the yield is 51.9%. (refer to Table 1)

Compound $I_4$: $^1$H-NMR (400 MHz, DMSO-$d_6$+$D_2$O) δ(ppm): 9.57 (1H), 8.38 (1H), 8.15 (1H), 7.90-7.84 (2H), 7.65-7.13 (8H), 6.85-6.73 (4H), 6.52 (1H), 6.38 (2H), 5.92 (1H), 5.73 (1H), 5.57 (1H), 5.40-5.18 (7H), 4.95 (1H), 4.80-4.31 (11H), 3.94-3.08 (31H), 2.97 (3H), 2.27-2.16 (6H), 2.00 (1H), 1.69-1.07 (71H), 0.87-0.86 (18H).

Example 5

Synthesis of the Compound $I_5$

At room temperature 35° C., water (5 ml) and acetonitrile (5 ml) are added into 100 ml eggplant-shaped flask, and then 1 mmol/ml morpholine (0.25 ml, 0.25 mmol) and DIEA (0.26 ml, 1.61 mmol) are added and stirred, then 1 mmol/ml formaldehyde solution (0.27 ml, 0.27 mmol) is added, and stirred for 15 min after the addition is completed. Compound (III) (500 mg, 0.23 mmol) ($R_1$=2-bromobenzyl, $R_2$=H, $R_3$=H, refer to the synthesis method of the Chinese Patent Application No. 201110070598.8) and DIEA (0.26 ml, 1.61 mmol) are added into the above solution, and stirred at room temperature for 3 h after the addition is completed. 70 ml acetone is added thereto under stirring to produce white insoluble precipitate and then filtered to obtain a filter cake, the filter cake is washed with acetone to produce a white solid, and purified by preparative HPLC, using an aqueous solution containing 0.1% HCOOH and methanol as a mobile phase to gradient elution with detection wavelength of 240 nm and 280 nm, a flow rate 22 ml/min. The fractions are concentrated under a reduced pressure to about 20 ml, and then adjusted to pH 6-7 with saturated sodium bicarbonate solution, and extracted by adding an equal volume of n-butanol, and an organic layer is separated and washed with water (10 ml×2), and evaporated to dryness solvent under a reduced pressure to produce a residue, the residue is stirred overnight after adding methylene chloride, filtered, and dried to obtain 30 mg compound $I_5$ at 45° C. (free base, solid brown powder), and the yield is 10.0%. (refer to Table 1)

Compound $I_5$: $^1$H-NMR (400 MHz, DMSO-$d_6$+$D_2$O) δ(ppm): 7.82 (2H), 7.65-7.11 (7H), 6.77 (2H), 6.51-6.47 (1H), 6.32 (2H), 5.61-5.59 (2H), 5.32 (3H), 5.18-5.12 (2H), 4.94 (1H), 4.87 (1H), 4.72-4.60 (3H), 4.48-4.09 (7H), 3.65-2.85 (9H), 2.33-2.00 (6H), 1.93 (2H), 1.77-1.40 (9H), 1.39-1.12 (11H), 1.05-1.03 (6H), 0.96-0.80 (6H).

The synthesis method of compound $I_8$, compound $I_9$, compound $I_{12}$, compound $I_{13}$ is the same as that of Example 5, but each of them selects different compound (III), wherein, $R_2$, $R_3$ are hydrogen, $R_1$ is 3-bromobenzyl, 4-bromobenzyl, 4-methoxybenzyl, or 4-isopropylbenzyl. (refer to Table 1)

Compound $I_8$: $^1$H-NMR (400 MHz, DMSO-$d_6$+$D_2$O) δ(ppm): 7.83 (2H), 7.59 (2H), 7.43-7.34 (3H), 7.21 (3H), 6.78 (2H), 6.59 (1H), 6.43 (1H), 5.80-5.54 (2H), 5.32 (3H), 5.18-5.11 (3H), 4.94 (1H), 4.86 (1H), 4.75 (2H), 4.40-3.95 (5H), 3.55-3.38 (5H), 3.37 (4H), 3.12-3.00 (2H), 2.27 (5H), 1.93 (2H), 1.70-1.55 (3H), 1.40 (4H), 1.36-1.04 (10H), 0.87-0.81 (6H).

Compound $I_9$: $^1$H-NMR (400 MHz, DMSO-$d_6$+$D_2$O) δ(ppm): 7.83 (2H), 7.59 (2H), 7.37 (3H), 7.20 (3H), 6.78 (3H), 6.59 (1H), 6.33 (2H), 5.54 (1H), 5.37-5.32 (2H), 5.18-5.11 (2H), 4.95 (1H), 4.85 (1H), 4.74 (1H), 4.49-4.26 (5H), 3.60-2.95 (12H), 2.27 (5H), 1.93 (2H), 1.68-1.39 (6H), 1.38-1.04 (10H), 0.87-0.82 (6H).

Compound $I_{12}$: $^1$H-NMR (400 MHz, DMSO-$d_6$+$D_2$O) δ(ppm): 7.81 (2H), 7.59 (2H), 7.39 (2H), 7.20 (3H), 6.78 (3H), 6.54 (1H), 6.32 (2H), 5.53 (2H), 5.32 (3H), 5.17-5.11 (2H), 4.94-4.86 (2H), 4.73-4.48 (2H), 4.37 (1H), 4.36-4.09 (4H), 3.68-3.07 (13H), 2.33 (4H), 2.01 (2H), 1.92 (2H), 1.71-1.50 (4H), 1.44-1.12 (14H), 1.03 (3H), 0.85-0.80 (6H).

Compound $I_{13}$: $^1$H-NMR (400 MHz, DMSO-$d_6$+$D_2$O) δ(ppm): 7.85 (2H), 7.60 (1H), 7.44 (2H), 7.36-7.10 (5H), 6.80 (3H), 6.59 (1H), 6.35 (1H), 5.64 (1H), 5.59 (1H), 5.40-5.33 (3H), 5.18 (2H), 4.95 (1H), 4.86 (1H), 4.76 (2H), 4.60-3.97 (5H), 3.28-2.68 (6H), 2.28 (5H), 1.91 (2H), 1.70-1.61 (4H), 1.48 (3H), 1.24-1.12 (12H), 0.88-0.84 (6H).

Example 6

Synthesis of the Compound $I_6$

At room temperature 20° C., water (5 ml) and acetonitrile (5 ml) are added into 100 ml eggplant-shaped flask, and then 1 mmol/ml diethylamine solution (0.25 ml, 0.25 mmol) and DIEA (0.26 ml, 1.61 mmol) are added under stirring, and afterwards 1 mmol/ml formaldehyde solution (0.25 ml, 0.25 mmol) is added into the solution under stirring for 15 min after the addition is completed. Compound (III) (500 mg, 0.23 mmol) ($R_1$=2-bromobenzyl, $R_2$=H, $R_3$=H, refer to the synthesis method of the Chinese Patent Application No. 201110070598.8), and DIEA (0.26 ml, 1.61 mmol) are added into the above solution, and stirred for 3 h at room temperature after the addition is completed. 70 ml acetone is added thereto under stirring to produce white insoluble precipitate and then filtered to obtain a filter cake, the filter cake is washed with acetone to obtain a white solid, then purified by preparative HPLC by using an aqueous solution containing 0.1% HCOOH and methanol as a mobile phase to gradient elution with detection wavelength of 240 nm and 280 nm, a flow rate is 22 ml/min. The fractions are concentrated under a reduced pressure to about 20 ml, and then adjusted to pH 6-7 with a saturated sodium bicarbonate solution, and extracted by adding an equal volume of n-butanol, an organic layer is separated and washed with water (10 ml×2), and evaporated to dryness solvent under a reduced pressure, the residue is stirred overnight after adding methylene chloride, filtered, and dried at 45° C. to obtain compound $I_6$ 30 mg (free base, white powder), the yield is 10.0%. (refer to Table 1)

Compound $I_6$: $^1$H-NMR (400 MHz, DMSO-$d_6$+$D_2O$) δ(ppm): 7.89 (2H), 7.58-7.13 (8H), 6.76-6.69 (2H), 6.54 (1H), 6.40-6.12 (1H), 5.71-5.45 (2H), 5.34-5.11 (6H), 4.94-4.63 (5H), 4.48-4.21 (6H), 3.40-2.83 (9H), 2.33-2.00 (6H), 2.00-1.60 (6H), 1.47-1.20 (10H), 1.17-1.03 (6H), 0.97-0.88 (6H).

And the synthesis method of Compound $I_{10}$ is the same as that of Example 6, but each of them selects different compounds (III), wherein, $R_1$ is 4-bromophenyl, $R_2$ is hydrogen, $R_3$ is hydrogen. (refer to Table 1)

Compound $I_{10}$: $^1$H-NMR (400 MHz, DMSO-$d_6$+$D_2O$) δ(ppm): 7.91-7.84 (2H), 7.58 (2H), 7.40 (3H), 7.21-7.00 (3H), 6.77 (2H), 6.58 (1H), 6.34 (1H), 5.70-5.55 (2H), 5.38-5.32 (2H), 5.19-5.11 (2H), 4.94 (1H), 4.87 (1H), 4.73 (2H), 4.49-3.95 (7H), 3.46-2.99 (5H), 2.34 (5H), 1.94 (2H), 1.70-1.30 (6H), 1.21 (8H), 1.04-0.98 (6H), 0.88-0.82 (6H).

Example 7

Synthesis of the Compound $I_7$

At room temperature 25° C., water (5 ml) and acetonitrile (5 ml) is added into 100 ml eggplant-shaped flask, n-butylamine solution 1 mmol/ml (0.25 ml, 0.25 mmol) and DIEA (0.26 ml, 1.61 mmol) is added under stirring, and then 1 mmol/ml formaldehyde solution (0.25 ml, 0.25 mmol) is added and stirred for 15 min after the addition is completed. Compound (III) (500 mg, 0.23 mmol) ($R_1$=2-bromobenzyl, $R_2$=H, $R_3$=H, synthesis refer to the synthesis method of the Chinese Patent Application No. 201110070598.8), and DIEA (0.26 ml, 1.61 mmol) are added, and stirred for 3 h at room temperature after the addition is completed. 70 ml acetone is added thereto with stirring to produce white insoluble precipitate and then filtered to obtain a filter cake, the filter cake is washed with acetone to obtain a white solid, and purified by preparative HPLC by using an aqueous solution containing 0.1% HCOOH and methanol as a mobile phase to gradient elution with detection wavelength of 240 nm and 280 nm, a flow rate is 22 ml/min. The fractions are concentrated under a reduced pressure to about 20 ml, and then adjusted to pH 6-7 with saturated sodium bicarbonate solution, and extracted by adding an equal volume of n-butanol, and an organic layer is separated and then washed with water (10 ml×2), and evaporated to dryness solvent under a reduced pressure to produce a residue, the residue is stirred overnight after adding methylene chloride, filtered and dried at 45° C. to obtain compound $I_7$ 27 mg free base (white powder), the yield is 7.0%. (refer to Table 1)

Compound $I_7$: $^1$H-NMR (400 MHz, DMSO-$d_6$+$D_2O$) δ(ppm): 7.91 (1H), 7.79-7.11 (9H), 6.86-6.76 (3H), 6.49 (1H), 6.32 (1H), 5.52 (2H), 5.31-5.11 (3H), 5.20-5.00 (3H), 4.94 (1H), 4.85 (1H), 4.74-4.48 (4H), 4.34-4.10 (7H), 3.60-2.70 (9H), 2.33 (5H), 2.02-1.93 (2H), 1.77-1.60 (5H), 1.38 (5H), 1.20 (10H), 1.03 (5H), 0.85-0.80 (9H).

Compound $I_{11}$, $I_{14}$ is the same as that of Example 7, but each of them selects different compounds (III), wherein, R2, R3 are hydrogen, R1 is 4-bromo benzyl, or 4-isopropylbenzyl. (refer to Table 1)

Compound $I_{11}$: $^1$H-NMR (400 MHz, DMSO-$d_6$+$D_2O$) δ(ppm): 7.90-7.85 (2H), 7.38-7.23 (4H), 7.23-7.13 (3H), 6.76-6.69 (3H), 6.50 (1H), 6.33-6.31 (2H), 5.66 (1H), 5.55 (1H), 5.38-5.19 (5H), 4.84-4.73 (2H), 4.68-4.21 (7H), 3.30-2.94 (8H), 2.33-2.01 (5H), 2.00 (2H), 1.96-1.44 (9H), 1.21 (19H), 1.04-0.88 (6H), 0.88-0.82 (9H).

Compound $I_{14}$: $^1$H-NMR (400 MHz, DMSO-$d_6$+$D_2O$) δ(ppm): 7.89-7.80 (2H), 7.59 (1H), 7.40 (2H), 7.17-7.10 (4H), 6.78 (2H), 6.48 (1H), 6.32 (1H), 5.54 (1H), 5.34-5.19 (3H), 5.13-5.00 (2H), 4.95 (1H), 4.86 (1H), 4.75 (2H), 4.47-4.10 (4H), 3.50-3.00 (9H), 2.28 (5H), 1.94 (2H), 1.74-1.53 (4H), 1.39-1.37 (5H), 1.34-1.12 (16H), 0.85-0.81 (9H).

Example 8

Synthesis of the Compound $I_{15}$

At room temperature 22° C., water (5 ml) and acetonitrile (5 ml) are added into 100 ml eggplant-shaped flask, a n-butylamine solution 1 mmol/ml (0.22 ml, 0.22 mmol) and DIEA (0.2 ml, 1.26 mmol) are added under stirring, and then 1 mmol/ml formaldehyde solution is added (0.22 ml, 0.22 mmol), and then stirred for 15 min after the addition is completed. Compound (III) (400 mg, 0.20 mmol) ($R_1$=H, $R_2$=Fmoc-, $R_3$=H, refer to the synthesis method of the Chinese Patent Application No. 201110070598.8), and DIEA (0.2 ml, 1.26 mmol) are added into the flask and then stirred for 3 h at room temperature after the addition is completed. 70 ml acetone is added thereto under stirring to produce white insoluble precipitate and then filtered to obtain a filter cake, the filter cake is washed with acetone to obtain a white solid, then purified by preparative HPLC by using an aqueous solution containing 0.1% HCOOH and methanol as a mobile phase to gradient elution with detection wavelength of 240 nm and 280 nm, a flow rate 22 ml/min. The fractions are concentrated under reduced pressure to about 20 ml, washed with saturated sodium bicarbonate solution and then adjusted to pH 6-7, and extracted by adding an equal volume of n-butanol, and an organic layer is separated and then washed with water (10 ml×2), and evaporated to dryness solvent under a reduced pressure to produce a residue, the residue is stirred overnight after adding methylene chloride, filtered, dried at 45° C. to obtain compound $I_{15}$ 30 mg (free base, white powder), yield 10.0%. (refer to Table 1)

MS (ESI): Compound of formula $I_{15}$ is $C_{93}H_{109}Cl_2N_{11}O_{28}$, its calculated molecular weight is 1897. Mass spectrum has m/z 1898.31 (M+H), m/z 1920.28 (M+Na). m/z 1899 (M+2), 1900 (M+2+H), 1901 (M+4), is the isotope peaks.

The synthesis of the compound $I_{16}$ is the same as that of Example 8, but morpholine is selected instead of n-butylamine solution, and have the same synthetic substrate and method. (refer to Table 1)

Compound $I_{16}$:

MS (ESI): Compound of formula $I_{16}$ is $C_{93}H_{107}Cl_2N_{11}O_{29}$, its calculated molecular weight is 1897. Mass spectrum has m/z 1912.34 (M+H, m/z 1935.31 (M+Na. m/z 1913.32 (M+2, 1914.30 (M+2+H, 1915.31 (M+4) is the isotope peaks.

Example 9

Synthesis of the Compound $II_1$

In an ice-water bath 0° C., water (3 ml) and acetonitrile (3 ml) are added into a 50 ml eggplant-shaped flask, n-butylamine solution 1 mmol/ml (0.12 ml, 1.2 mmol) and 1 mmol/ml formaldehyde solution (0.25 ml, 1.0 mmol) are added, and then stirred for 15 min. Compound (III) (320 mg, 0.2 mmol) (R1=H, R2=H, R3=H, refer to the synthesis method of the Chinese Patent Publication No. CN 101928331 A) is added after the addition is completed, the ice bath is removed and stirred for 3 h at room temperature 15-25° C. 70 ml acetone is added thereto under stirring to produce white insoluble precipitate and then filtered to obtain a filter cake, the filter cake is washed with acetone to obtain a white solid, purified by preparative HPLC, by using an aqueous solution containing 0.1% HCOOH and methanol as a mobile phase to gradient elution with detection wavelength of 240 nm and 280 nm, a flow rate 22 ml/min. The fractions are concentrated under reduced pressure to about 20 ml, and then adjusted to pH 6-7 with saturated sodium bicarbonate solution, and extracted by adding an equal volume n-butanol, and an organic layer is separated and washed with water (10 ml×2), and evaporated to dryness solvent under a reduced pressure to produce a residue, the residue is stirred overnight after adding methylene chloride, filtered, and dried at 45° C. to obtain compound $II_1$ 101 mg, the yield is 30.1%. (refer to Table 2)

MS (ESI): Compound of formula $II_1$ is $C_{79}H_{99}Cl_2N_{11}O_{26}$, its calculated molecular weight is 1687. Mass spectrum has m/z 1688 (M+H, m/z 1720 (M+Na. m/z 1,689 (M+2, 1690 (M+2+H, 1691 (M+4) is the isotope peaks.

$^1$H-NMR (400 MHz, DMSO-$d_6$+$D_2O$) δ(ppm): 7.84-7.56 (3H), 7.42-7.34 (1H), 7.14-7.04 (3H), 6.69-6.45 (3H), 6.04 (1H), 5.67-5.31 (7H), 5.07 (2H), 4.82 (2H), 4.31 (4H), 4.04 (1H), 3.75-3.32 (7H), 3.09-3.00 (3H), 2.58-2.45 (6H), 2.33-2.07 (4H), 1.72-1.10 (19H), 0.97-0.72 (9H).

Example 10

Synthesis of the Compound $II_2$

At room temperature 25° C., water (5 ml) and acetonitrile (5 ml) are added into an 100 ml eggplant-shaped flask, a diethylamine solution 1 mmol/ml (0.23 ml, 0.23 mmol) and DIEA solution (0.26 ml, 1.61 mmol) are added under stirring, and then 1 mmol/ml formaldehyde solution is added (0.23 ml, 0.23 mmol), and stirred for 15 min after the addition is completed. Compound (III) (500 mg, 0.23 mmol) ($R_1$=2-bromobenzyl, $R_2$=H, $R_3$=H, refer to the synthesis method of the Chinese Patent Application No. 201110070598.8) and DIEA (0.26 ml, 1.61 mmol) are added into the flask, and stirred for 3 h at room temperature after the addition is completed. 70 ml acetone is added thereto under stirring to produce white insoluble precipitate and then filtered to obtain a filter cake, the filter cake is washed with acetone to obtain a white solid, purified by preparative HPLC, by using an aqueous solution containing 0.1% HCOOH and methanol as a mobile phase to gradient elution with detection wavelength of 240 nm and 280 nm, a flow rate is 22 ml/min. The fractions are concentrated under reduced pressure to about 20 ml, and then adjusted to pH 6-7 with saturated sodium bicarbonate solution, and extracted by adding an equal volume n-butanol, and an organic layer is separated and washed with water (10 ml×2), and evaporated to dryness solvent under a reduced pressure to produce a residue, the residue is stirred overnight after adding methylene chloride, filtered, then dried at 45° C. to obtain Compound $II_2$ 40 mg (free base, white powder), the yield is 10.0%. (See Table 2)

MS (ESI): Compound of formula $II_2$ is $C_{86}H_{104}BrCl_2N_{11}O_{26}$, its calculated molecular weight is 1855. Mass spectrum has 1657 (M+H), m/z 1778 (M+Na). m/z 1857 (M+2, 1859 (M+4) is the isotope peaks.

$^1$H-NMR (400 MHz, DMSO-$d_6$+$D_2O$) δ(ppm): 7.89 (2H), 7.58-7.13 (8H), 6.76-6.69 (2H), 6.54 (1H), 6.40-6.12 (1H), 5.71-5.45 (2H), 5.34-5.11 (6H), 4.94-4.63 (5H), 4.48-4.21 (6H), 3.40-2.83 (9H), 2.33-2.00 (6H), 2.00-1.60 (6H), 1.47-1.20 (10H), 1.17-1.03 (6H), 0.97-0.88 (6H).

Synthesis method of the Compound $II_7$, $II_8$ is the same as that of Example 10, but each of them selects different compounds (III), wherein, R2, R3 are hydrogen, R1, is 4-bromo benzyl or 4-methoxybenzyl. (refer to Table 2)

Compound $II_7$: $^1$H-NMR (400 MHz, DMSO-$d_6$+$D_2O$) δ(ppm): 789 (2H), 7.57 (2H), 7.54-7.50 (3H), 7.26-7.11 (3H), 6.77-6.67 (2H), 6.55 (1H), 5.73 (1H), 5.63 (1H), 5.52 (1H), 5.38-5.11 (5H), 4.86 (1H), 4.72-4.52 (2H), 4.38 (1H), 4.36 (1H), 4.33 (1H), 4.23-4.04 (4H), 3.25-2.67 (7H), 2.34-2.01 (5H), 1.86 (2H), 1.77-1.35 (9H), 1.22 (7H), 1.20-1.00 (8H), 0.89-0.83 (6H).

Compound $II_8$: $^1$H-NMR (400 MHz, DMSO-$d_6$+$D_2O$) δ(ppm): 7.90 (2H), 7.59 (2H), 7.36-7.27 (2H), 7.22-7.14 (4H), 6.85-6.68 (4H), 6.56 (1H), 6.34 (1H), 5.74 (1H), 5.65 (1H), 5.55 (1H), 5.40-5.11 (5H), 4.87-4.74 (4H), 4.63 (1H), 4.50 (1H), 4.42 (1H), 4.35 (2H), 4.25-3.75 (4H), 3.65-3.10 (9H), 2.40-2.02 (5H), 1.94-1.60 (5H), 1.50-1.21 (12H), 1.00 (6H), 0.99-0.84 (6H).

Example 11

Synthesis of the Compound $II_4$

At room temperature 25° C., methanol (5 ml) and ethanol (5 ml) are added into a 100 ml eggplant-shaped flask, a diethylamine solution 1 mmol/ml (0.23 ml, 0.23 mmol) and DIEA (0.26 ml, 1.61 mmol) are added under stirring, and then 1 mmol/ml formaldehyde solution (0.69 ml, 0.69 mmol) is added and stirred for 15 min after the addition is completed. Compound (III) (500 mg, 0.23 mmol) ($R_1$=2-bromobenzyl, $R_2$=H, $R_3$=H, refer to the synthesis method of the Chinese Patent Application No. 201110070598.8), and DIEA (0.26 ml, 1.61 mmol) are added into the flask, and stirred for 3 h at room temperature after the addition is completed. 70 ml acetone is added thereto under stirring to produce white insoluble precipitate and then filtered to obtain a filter cake, the filter cake is washed with acetone to obtain a white solid, purified by preparative HPLC, by using an aqueous solution containing 0.1% HCOOH and methanol as a mobile phase to gradient elution with detection wavelength of 240 nm and 280 nm, a flow rate 22 ml/min. The fractions are concentrated under reduced pressure to about 20 ml, and then adjusted to pH 6-7 with saturated sodium bicarbonate solution, and extracted by adding an equal volume n-butanol, and an organic layer is separated and washed with water (10 ml×2), and evaporated to dryness solvent under a reduced pressure to produce a residue, the residue is stirred overnight after adding methylene chloride, filtered, then dried at 45° C. to obtain the compound II$_4$ 40 mg (free base, white powder), yield 10.0%. (refer to Table 2)

Compound II$_4$: $^1$H-NMR (400 MHz, DMSO-d$_6$+D$_2$O) δ(ppm): 7.87-7.60 (2H), 7.54-7.11 (6H), 7.12 (2H), 6.75 (2H), 6.50 (1H), 5.68-5.50 (2H), 5.33-5.00 (5H), 4.84-4.62 (4H), 4.47-4.06 (6H), 3.70-3.35 (8H), 3.25-2.84 (4H), 2.33 (5H), 2.02-1.46 (5H), 1.38-1.02 (18H), 0.86-0.80 (9H).

Example 12

Synthesis of the Compound II$_3$

At a temperature 35° C., water (5 ml) and acetonitrile (5 ml) are added into an 100 ml eggplant-shaped flask, a n-butylamine solution 1 mmol/ml (0.28 ml, 0.28 mmol) and DIEA (0.22 ml, 1.38 mmol) are added under stirring, and then 1 mmol/ml formaldehyde solution (1.38 ml, 1.38 mmol) is added, and stirred for 15 min after the addition is completed. Compound (III) (500 mg, 0.23 mmol) (R1=2-bromobenzyl, R2=H, R3=H, refer to the synthesis method of the Chinese Patent Application No. 201110070598.8), and DIEA (0.22 ml, 1.38 mmol) are added into the flask, stirred for 3 h at room temperature after the addition is completed. 70 ml acetone is added thereto under stirring to produce white insoluble precipitate and then filtered to obtain a filter cake, the filter cake is washed with acetone to obtain a white solid, purified by preparative HPLC, by using an aqueous solution containing 0.1% HCOOH and methanol as a mobile phase to gradient elution with detection wavelength of 240 nm and 280 nm, a flow rate 22 ml/min. The fractions are concentrated under reduced pressure to about 20 ml, and then adjusted to pH 6-7 with saturated sodium bicarbonate solution, and extracted by adding an equal volume n-butanol, and an organic layer is separated and washed with water (10 ml×2), and evaporated to dryness solvent under a reduced pressure to produce a residue, the residue is stirred overnight after adding methylene chloride, filtered, then dried at 45° C. to obtain the compound II$_3$ 40 mg (free base, white powder), the yield is 10.5%. (refer to Table 2)$^1$H-NMR (400 MHz, DMSO-d$_6$+D$_2$O) δ(ppm): 7.88-7.83 (2H), 7.59-7.12 (9H), 6.78 (2H), 6.70-6.53 (2H), 5.73-5.54 (3H), 5.38-5.12 (6H), 4.94-4.63 (5H), 4.49-4.05 (8H), 3.44-2.84 (6H), 2.34 (5H), 2.13-1.68 (3H), 1.61-1.43 (6H), 1.38-1.22 (6H), 1.05-1.04 (7H), 0.99-0.88 (6H).

Synthesis method of the compound II$_5$ is the same as that of Example 12, but each of them selects different compounds (III), wherein, R1 is 3-bromobenzyl, R2 is hydrogen, R3 is hydrogen. (refer to Table 2)

Compound II$_5$: $^1$H-NMR (400 MHz, DMSO-d$_6$+D$_2$O) δ(ppm): 7.87-7.60 (2H), 7.54-7.11 (6H), 7.12 (2H), 6.75 (2H), 6.50 (1H), 5.68-5.50 (2H), 5.33-5.00 (5H), 4.84-4.62 (4H), 4.47-4.06 (6H), 3.70-3.35 (8H), 3.25-2.84 (4H), 2.33 (5H), 2.02-1.46 (5H), 1.38-1.02 (18H), 0.86-0.80 (9H).

Example 13

Synthesis of the Compound II$_6$

At room temperature 20° C., methanol (6 ml) and n-butanol (3 ml) are added into an 100 ml eggplant-shaped flask, 1 mmol/ml morpholine (0.46 ml, 0.46 mmol) and DIEA (0.26 ml, 1.61 mmol) are added under stirring, and then 1 mmol/ml formaldehyde solution (2.3 ml, 2.3 mmol) is added, stirred for 15 min after the addition is completed. the compound (III) (500 mg, 0.23 mmol) (R1=3-bromo-benzyl, R2=H, R3=H, refer to the synthesis method of the Chinese Patent Application No. 201110070598.8) and DIEA (0.26 ml, 1.61 mmol) are added, and stirred for 3 h at room temperature after the addition is completed. 70 ml acetone is added thereto under stirring to produce white insoluble precipitate and then filtered to obtain a filter cake, the filter cake is washed with acetone to obtain a white solid, then purified by preparative HPLC, by using an aqueous solution containing 0.1% HCOOH and methanol as a mobile phase to gradient elution with detection wavelength of 240 nm and 280 nm, a flow rate 22 ml/min. The fractions are concentrated under reduced pressure to about 20 ml, and then adjusted to pH 6-7 with saturated sodium bicarbonate solution, and extracted by adding an equal volume n-butanol, and an organic layer is separated and washed with water (10 ml×2), and evaporated to dryness solvent under a reduced pressure to produce a residue, the residue is stirred overnight after adding methylene chloride, filtered, then dried at 45° C. to the solution is the compound II$_6$ 40 mg (free base, white powder), the yield is 10.5%. (refer to Table 2)

Compound II$_6$: $^1$H-NMR (400 MHz, DMSO-d$_6$+D$_2$O) δ(ppm): 7.89 (2H), 7.57-7.12 (7H), 6.76-6.69 (2H), 6.52 (1H), 6.33 (1H), 5.75-5.54 (2H), 5.37-5.06 (4H), 5.00-4.49 (3H), 4.40-3.90 (5H), 3.25-3.10 (5H), 2.82-2.70 (2H), 2.40-2.00 (6H), 1.85 (2H), 1.67-1.04 (16H), 0.88 (6H).

Synthesis method of compound II$_9$ is the same as that of Example 13, but each of them selects different compounds (III), wherein, R1 is 4-iso-benzyl, R2 is hydrogen, R3 is hydrogen. (refer to Table 2)

Compound II$_9$: $^1$H-NMR (400 MHz, DMSO-d$_6$+D$_2$O) δ(ppm): 7.85-7.79 (2H), 7.54 (4H), 7.30 (4H), 7.00-6.90 (2H), 6.58 (2H), 5.96 (1H), 5.79 (1H), 5.60-5.31 (4H), 5.15 (2H), 5.00-4.79 (4H), 4.66-4.43 (4H), 4.00-3.26 (14H), 2.70-2.02 (10H), 2.00-1.42 (8H), 1.20-1.10 (12H), 0.86 (6H).

In the above Examples 1~13, the following abbreviations have their respective meanings. Undefined abbreviations have their generally accepted meaning, unless noted otherwise, all room temperature is referred to as 20° C.~30° C.

DMF N,N-dimethyl-Formamide
DIEA N,N-Diisopropylethylamine
Fmoc- Fluorenylmethoxycarbonyl
TFA Trifluoroacetic acid
HPLC High Performance Liquid Chromatography
MIC minimum inhibitory concentration Refer to relevant data of compounds of formula (I) or (III) of some examples in Table 1 and Table 2

Purified condition by preparative HPLC in Example 1~13 includes Chromatographic Column Sepax BR-C$_{18}$ 21.2×100 mm (5 μm), gradient elution, wherein the composition of a mobile phase is as follows.

| Time (min) | Methyl Alcohol | 0.1% methanoic acid |
|---|---|---|
| 0 | 5 | 95 |
| 20 | 30 | 70 |

Detection wavelength is 240 nm and 280 nm. Organic solvents of needed fractions are removed under reduced pressure, and then adjusted to pH 6-7 with saturated aqueous sodium bicarbonate, and extracted with n-butanol, washed with water, and evaporated alcohol under reduced pressure, and dried to obtain the product. The yield of the present invention is referred to as a molar yield.

TABLE 1

Compound of formula (I)

| NO. | R₁ | R₂ | R₃ | NR₄R₅ | Formula | $[\alpha]_D^{25}$ C = 0.1 | ESI |
|---|---|---|---|---|---|---|---|
| I₁ | H | H | H | —NH—CH₂—PO₃H | $C_{75}H_{94}Cl_2N_{11}O_{27}P$ | $-52^a$ | 1714.68 (M + H) |
| I₂ | H | H | H | —N(morpholine) | $C_{78}H_{97}Cl_2N_{11}O_{27}$ | $-44^a$ | 1712.12 (M + Na) |
| I₃ | H | H | H | NH—n-C₄H₉ | $C_{75}H_{94}Cl_2N_{11}O_{27}$ | $-54^a$ | 1700.27 (M + Na) |
| I₄ | n-C₁₀H₂₁ | n-C₁₀H₂₁ | n-C₁₀H₂₁ | NH—n-C₄H₉ | $C_{108}H_{159}Cl_2N_{11}O_{26}$ | $-76^a$ | 2097.95 (M + H) |
| I₅ | —CH₂—(2-Br-C₆H₄) | H | H | —N(morpholine) | $C_{85}H_{102}BrCl_2N_{11}O_{27}$ | $-78^b$ | 1858.53 (M + H) |
| I₆ | —CH₂—(2-Br-C₆H₄) | H | H | —N(C₂H₅)₂ | $C_{85}H_{104}BrCl_2N_{11}O_{26}$ | $-58^b$ | 1866.62 (M + Na) |
| I₇ | —CH₂—(2-Br-C₆H₄) | H | H | —NH—n-C₄H₉ | $C_{85}H_{104}BrCl_2N_{11}O_{26}$ | $-41^c$ | 1866.66 (M + Na) |
| I₈ | —CH₂—(3-Br-C₆H₄) | H | H | —N(morpholine) | $C_{85}H_{102}BrCl_2N_{11}O_{27}$ | $-48^c$ | 1880.46 (M + Na) |
| I₉ | —CH₂—(4-Br-C₆H₄) | H | H | —N(morpholine) | $C_{85}H_{102}BrCl_2N_{11}O_{27}$ | $-71^c$ | 1880.55 (M + Na) |
| I₁₀ | —CH₂—(4-Br-C₆H₄) | H | H | —N(C₂H₅)₂ | $C_{85}H_{104}BrCl_2N_{11}O_{26}$ | $-35^b$ | 1866.61 (M + Na) |
| I₁₁ | —CH₂—(4-Br-C₆H₄) | H | H | —NH—n-C₄H₉ | $C_{85}H_{104}BrCl_2N_{11}O_{26}$ | $-50^c$ | 1866.54 (M + Na) |
| I₁₂ | —CH₂—(4-OCH₃-C₆H₄) | H | H | —N(morpholine) | $C_{86}H_{105}Cl_2N_{11}O_{28}$ | $-18^b$ | 1810.72 (M + H) |
| I₁₃ | —CH₂—(4-iPr-C₆H₄) | H | H | —N(morpholine) | $C_{88}H_{109}Cl_2N_{11}O_{27}$ | $-44^c$ | 1822.59 (M + H) |
| I₁₄ | —CH₂—(4-iPr-C₆H₄) | H | H | —NH—n-C₄H₉ | $C_{88}H_{111}Cl_2N_{11}O_{26}$ | $-60^b$ | 1808.80 (M + H) |
| I₁₅ | H | Fmoc- | H | —NH—n-C₄H₉ | $C_{93}H_{109}Cl_2N_{11}O_{28}$ | $-50^b$ | 1920.28 (M + Na) |

TABLE 1-continued

Compound of formula (I)

| NO. | R₁ | R₂ | R₃ | NR₄R₅ | Formula | $[\alpha]_D^{25}$ C = 0.1 | ESI |
|---|---|---|---|---|---|---|---|
| I₁₆ | H | Fmoc- | H | 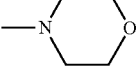 | $C_{93}H_{107}Cl_2N_{11}O_{29}$ | $-55^b$ | 1935.31 (M + Na) |

Note:
$^a$is a solvent of water,
$^b$is a solvent of DMF,
$^c$is a solvent of methanol

TABLE 2

Compound of formula (II)

| NO. | R₁ | NR₄R₅ | Formula | $[\alpha]_D^{25}$ C = 0.1 | ESI |
|---|---|---|---|---|---|
| II₁ | H | —NH—n-C₄H₉ | $C_{79}H_{99}Cl_2N_{11}O_{26}$ | $-76^a$ | 1688.67 (M + H) |
| II₂ | 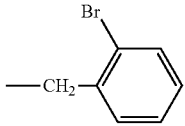 | —N(C₂H₅)₂ | $C_{86}H_{104}BrCl_2N_{11}O_{26}$ | $-32^a$ | 1857.61 (M + 2) |
| II₃ | 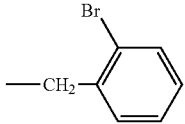 | —NH—n-C₄H₉ | $C_{86}H_{104}BrCl_2N_{11}O_{26}$ | $-47^b$ | 1878.51 (M + Na) |
| II₄ | 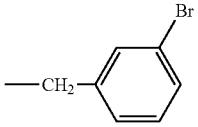 | —N(C₂H₅)₂ | $C_{86}H_{104}BrCl_2N_{11}O_{26}$ | $-64^a$ | 1856.47 (M + H) |
| II₅ | 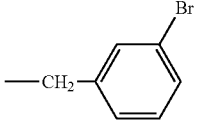 | —NH—n-C₄H₉ | $C_{86}H_{104}BrCl_2N_{11}O_{26}$ | $-53^b$ | 1856.70 (M + H) |
| II₆ | 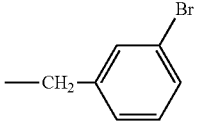 | 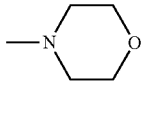 | $C_{86}H_{102}BrCl_2N_{11}O_{27}$ | $-32^b$ | 1893.15 (M + Na) |
| II₇ | 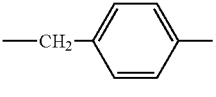 | —N(C₂H₅)₂ | $C_{86}H_{104}BrCl_2N_{11}O_{26}$ | $-51^b$ | 1878.62 (M + Na) |
| II₈ | 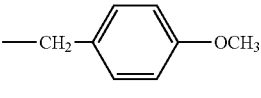 | —N(C₂H₅)₂ | $C_{87}H_{107}Cl_2N_{11}O_{27}$ | $-18^a$ | 1808.64 (M + H) |
| II₉ | 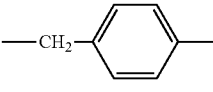 | 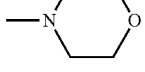 | $C_{89}H_{109}Cl_2N_{11}O_{27}$ | $-34^b$ | 1834.70 (M + H) |

Note:
$^a$is a solvent of water,
$^b$is a solvent of DMF,
$^c$is a solvent of methanol

Effects of Examples

Testing results of in vitro antibacterial activity of some target compounds of the present invention are as follows:
1. Testing Method:
Drugs: firstly being dissolved in DMSO, and then being diluted to an appropriate concentration with sterile water, and afterwards successively being diluted for twice.
Determination: referencing the standard of CSSI 2008 version, using a agar two times dilution method, determine the minimum inhibitory concentration (MIC values).
2. Testing Bacterial Strain
Feces enterococci (VSE clinical isolates: MEFA 0039); *Streptococcus pneumoniae* (PISP: ATCC 49619).
3. Positive Control Drug is Vancomycin Hydrochloride.
MIC values of some compound are shown in Table 3.

TABLE 3

| MIC Values of Compounds (μg/ml) | | |
|---|---|---|
| Compound | Enterococci | Streptococcus pneumoniae |
| vancomycin hydrochloride | 0.25 | 0.125 |
| $I_1$ | 0.5 | 0.125 |
| $I_2$ | 0.5 | 0.063 |
| $I_3$ | 0.5 | 0.25 |
| $I_4$ | >8 | >8 |
| $I_5$ | 0.25 | 0.125 |
| $I_6$ | 1 | 0.25 |
| $I_7$ | 1 | 0.5 |
| $I_8$ | 0.25 | 0.063 |
| $I_9$ | 0.25 | ≤0.031 |
| $I_{10}$ | 2 | 0.25 |
| $I_{11}$ | 1 | 0.25 |
| $I_{12}$ | 2 | 1 |
| $I_{13}$ | 1 | 0.25 |
| $I_{14}$ | 0.5 | ≤0.031 |
| $II_1$ | 0.25 | 0.125 |
| $II_2$ | 2 | 0.5 |
| $II_3$ | 2 | 0.25 |
| $II_4$ | 2 | 0.25 |
| $II_5$ | 1 | 0.25 |
| $II_6$ | 2 | 0.25 |
| $II_7$ | 1 | 0.25 |
| $II_8$ | 1 | 0.25 |
| $II_9$ | 1 | 0.25 |

It can be seen from Table 3, the activity of series compound I is obviously superior to the activity of series compound II. Compared with the positive control of vancomycin, the activity of series compounds I against enterococci is comparable to vancomycin or is weaker than vancomycin; and the activity against *Streptococcus pneumoniae* is superior to vancomycin. Wherein, the activity of compounds $I_{14}$ and $I_9$ against *streptococcus pneumoniae* is more four times than vancomycin. So it is worthy for further modification and pharmacological activity.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:
1. A glycopeptide compound or pharmaceutically acceptable salt thereof of Formula (II),

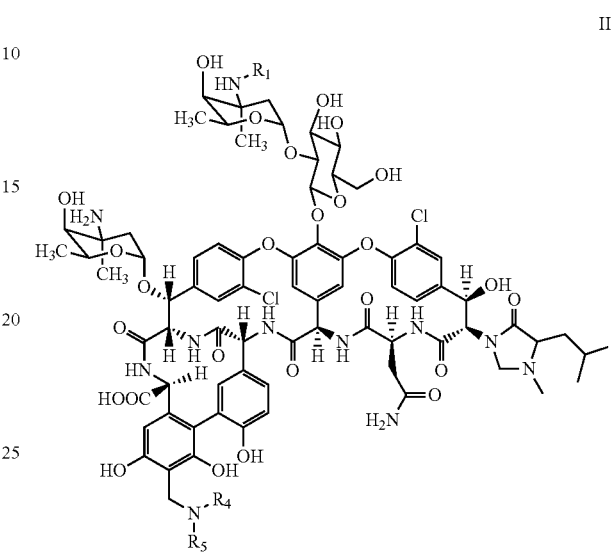

II wherein:
R1 is a mono-substituted benzyl substituted by halogen, methoxy or isopropyl;
a group of NR4R5 is diethylamino, n-butylamino, or morpholino.

2. The glycopeptide compound or pharmaceutically acceptable salt thereof according to claim 1, wherein the mono-substituted benzyl is 2-bromobenzyl, 3-bromophenyl, 4-bromobenzyl, 4-isopropylbenzyl or 4-methoxybenzyl.

3. The glycopeptide compound or pharmaceutically acceptable salt thereof according to claim 1, wherein a hydroxyl at position 4 of amino acid sugar at position 6 of peptide backbone is a axial bond.

4. A pharmaceutical composition, comprising a therapeutically effective amount of glycopeptide compounds or pharmaceutically acceptable salts thereof and a pharmaceutically acceptable carrier according to claim 1.

5. The pharmaceutical composition according to claim 4, wherein the pharmaceutical composition comprises 0.1 wt. %-99.5 wt. % of the glycopeptide compound or pharmaceutically acceptable salt thereof.

6. The pharmaceutical composition according to claim 5, wherein the pharmaceutical composition comprises, preferably, 0.5 wt. %-90 wt. % of the glycopeptide compound or pharmaceutically acceptable salt thereof.

7. A pharmaceutical composition, comprising a therapeutically effective amount of glycopeptide compounds or pharmaceutically acceptable salts thereof and a pharmaceutically acceptable carrier according to claim 2.

8. The pharmaceutical composition according to claim 7, wherein the pharmaceutical composition comprises 0.1 wt. %-99.5 wt. % of the glycopeptide compound or pharmaceutically acceptable salt thereof.

9. The pharmaceutical composition according to claim 8, wherein the pharmaceutical composition comprises 0.5 wt. %-90 wt. % of the glycopeptide compound or pharmaceutically acceptable salt thereof.

10. A pharmaceutical composition, comprising a therapeutically effective amount of glycopeptide compounds or pharmaceutically acceptable salts thereof and a pharmaceutically acceptable carrier according to claim 3.

11. The pharmaceutical composition according to claim 10, wherein the pharmaceutical composition comprises 0.1 wt. %-99.5 wt. % of the glycopeptide compound or pharmaceutically acceptable salt thereof.

12. The pharmaceutical composition according to claim 11, wherein the pharmaceutical composition comprises 0.5 wt. %-90 wt. % of the glycopeptide compound or pharmaceutically acceptable salt thereof.

\* \* \* \* \*